United States Patent [19]
Lindegren

[11] Patent Number: 5,306,292
[45] Date of Patent: Apr. 26, 1994

[54] HEART STIMULATION APPARATUS
[75] Inventor: Ulf Lindegren, Enskede, Sweden
[73] Assignee: Siemens-Elema AB, Solna, Sweden
[21] Appl. No.: 60,546
[22] Filed: May 13, 1993
[30] Foreign Application Priority Data
 May 25, 1992 [SE] Sweden ............... 92016401
 Aug. 28, 1992 [SE] Sweden ................. 9202479
[51] Int. Cl.⁵ ............................. A61N 1/368
[52] U.S. Cl. ..................................... 607/11
[58] Field of Search ............ 607/2, 11, 27, 116, 607/126, 127, 122; 128/642

[56] References Cited
U.S. PATENT DOCUMENTS

| | | | |
|---|---|---|---|
| 3,911,928 | 10/1975 | Lagergren | 607/122 |
| 4,217,913 | 8/1980 | Dutcher | 607/127 |
| 4,281,668 | 8/1981 | Richter et al. | 607/121 |
| 4,611,604 | 9/1986 | Botvidsson et al. | 607/122 |
| 4,628,934 | 12/1986 | Pohndorf et al. | 607/27 |
| 4,628,943 | 12/1986 | Miller | 607/127 |
| 4,662,382 | 5/1987 | Sluetz et al. | 607/126 |
| 4,760,852 | 8/1988 | Lekholm | 607/116 |
| 4,784,161 | 11/1988 | Skalsky et al. | 607/116 |
| 4,848,352 | 7/1989 | Pohndorf et al. | 128/642 |
| 4,955,382 | 9/1990 | Franz et al. | 128/642 |
| 4,964,407 | 10/1990 | Baker, Jr. et al. | 607/27 |
| 5,018,523 | 5/1991 | Bach, Jr. et al. | 607/2 |

Primary Examiner—William E. Kamm
Assistant Examiner—George Manuel
Attorney, Agent, or Firm—Hill, Steadman & Simpson

[57] ABSTRACT

A heart stimulation apparatus for intracardial stimulation of heart tissue has an electrode device with an electrode head provided at the distal end thereof, having at least a first conductive surface and a second conductive surface, a stimulation pulse generator and a switch for selectively connecting the conductive surface(s) to the stimulation pulse generator in any combination. In order to reduce the energy consumption, an autocapture unit is provided which automatically tests a number of possible combinations of conductive surfaces for stimulation and selects the combination providing the lowest stimulation threshold for connection to the pulse generator. A heart signal detector can also be provided to which the electrode surfaces are also connectable in any combination, with the autocapture unit selecting an optimal combination for sensing as well.

16 Claims, 5 Drawing Sheets

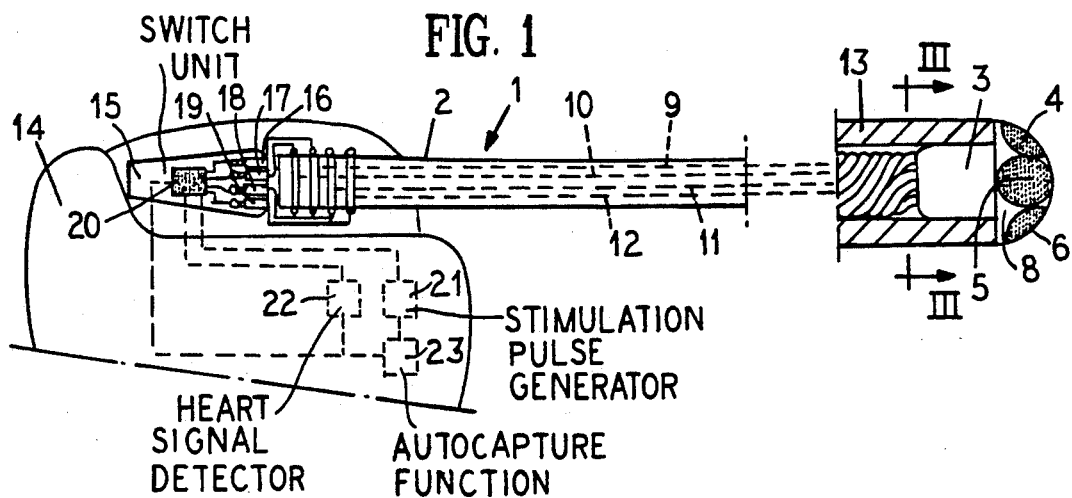
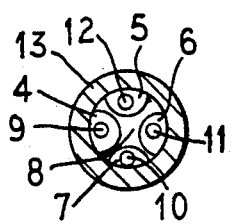
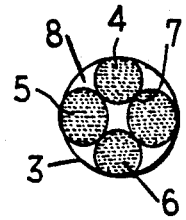
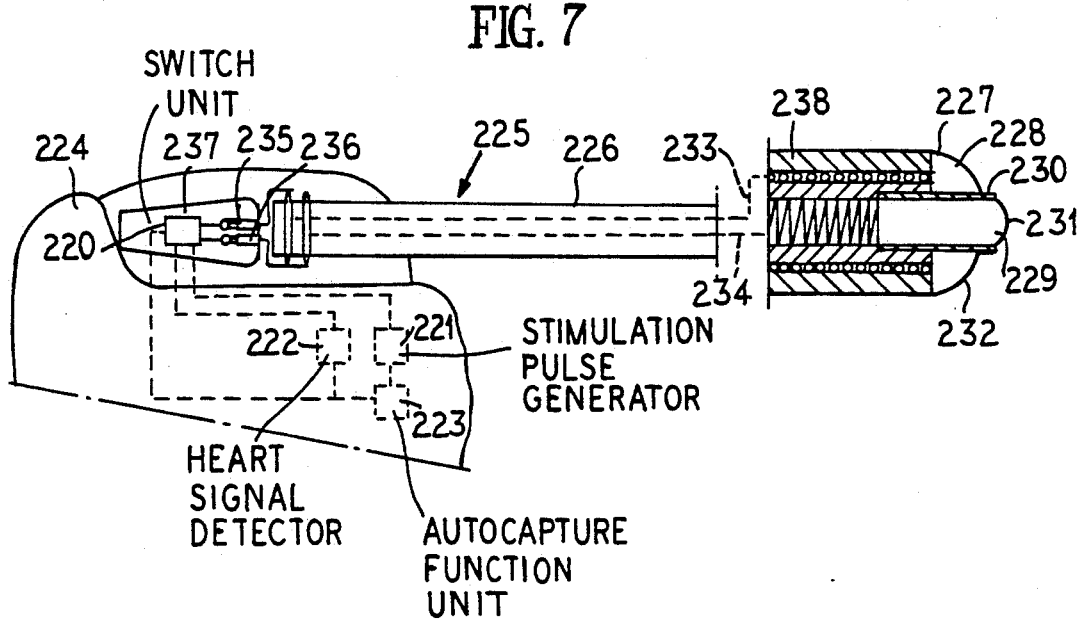

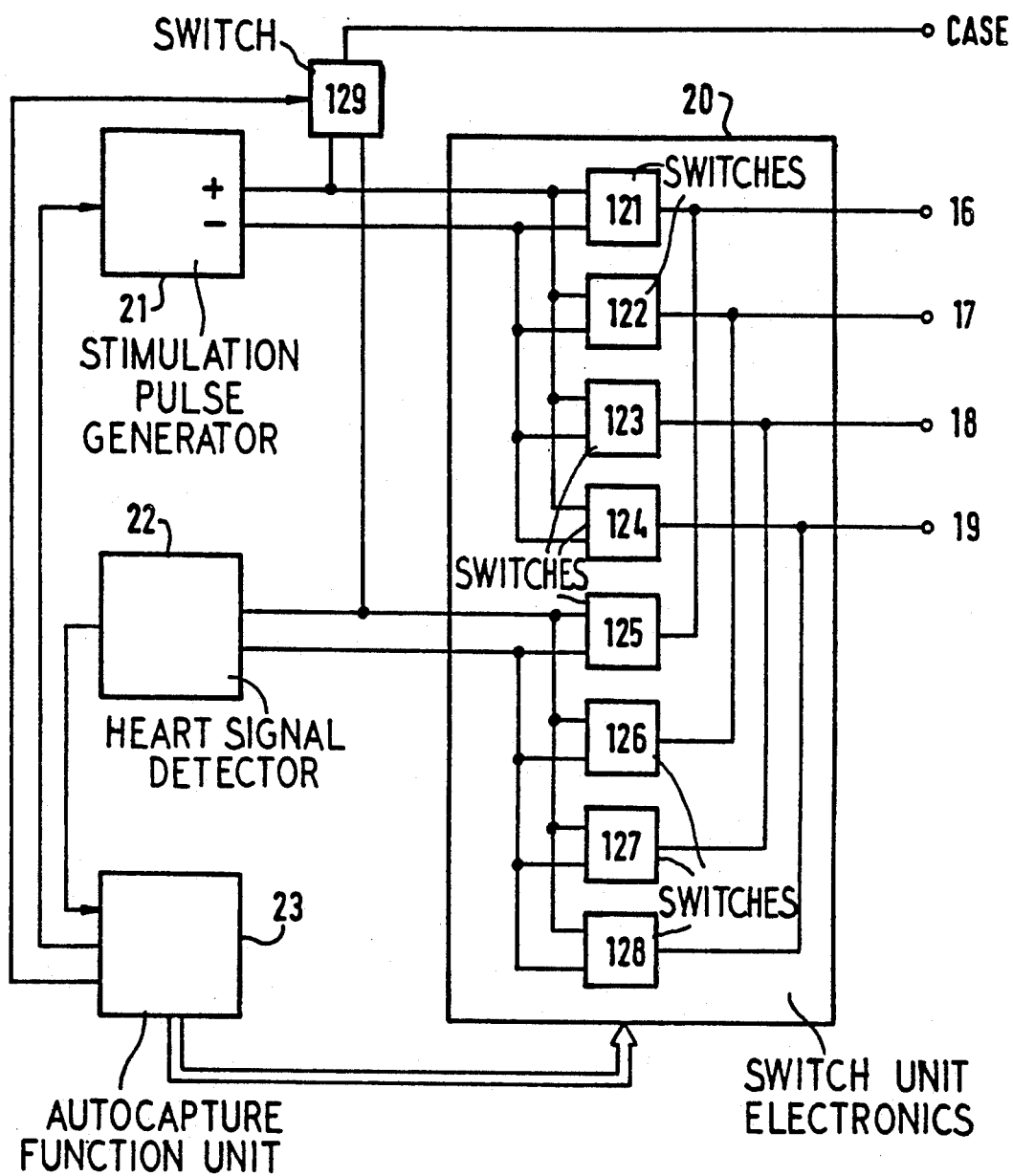

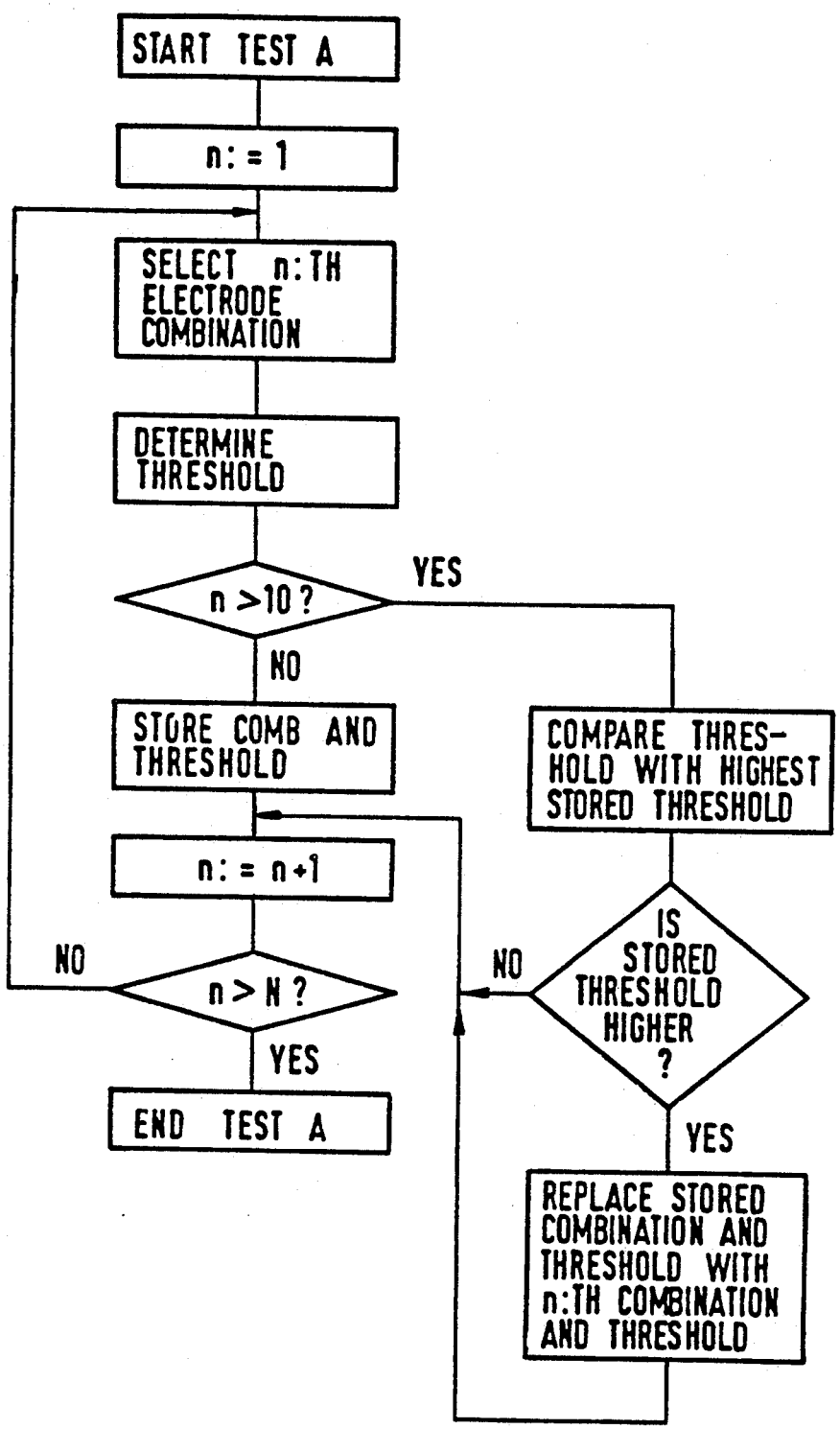

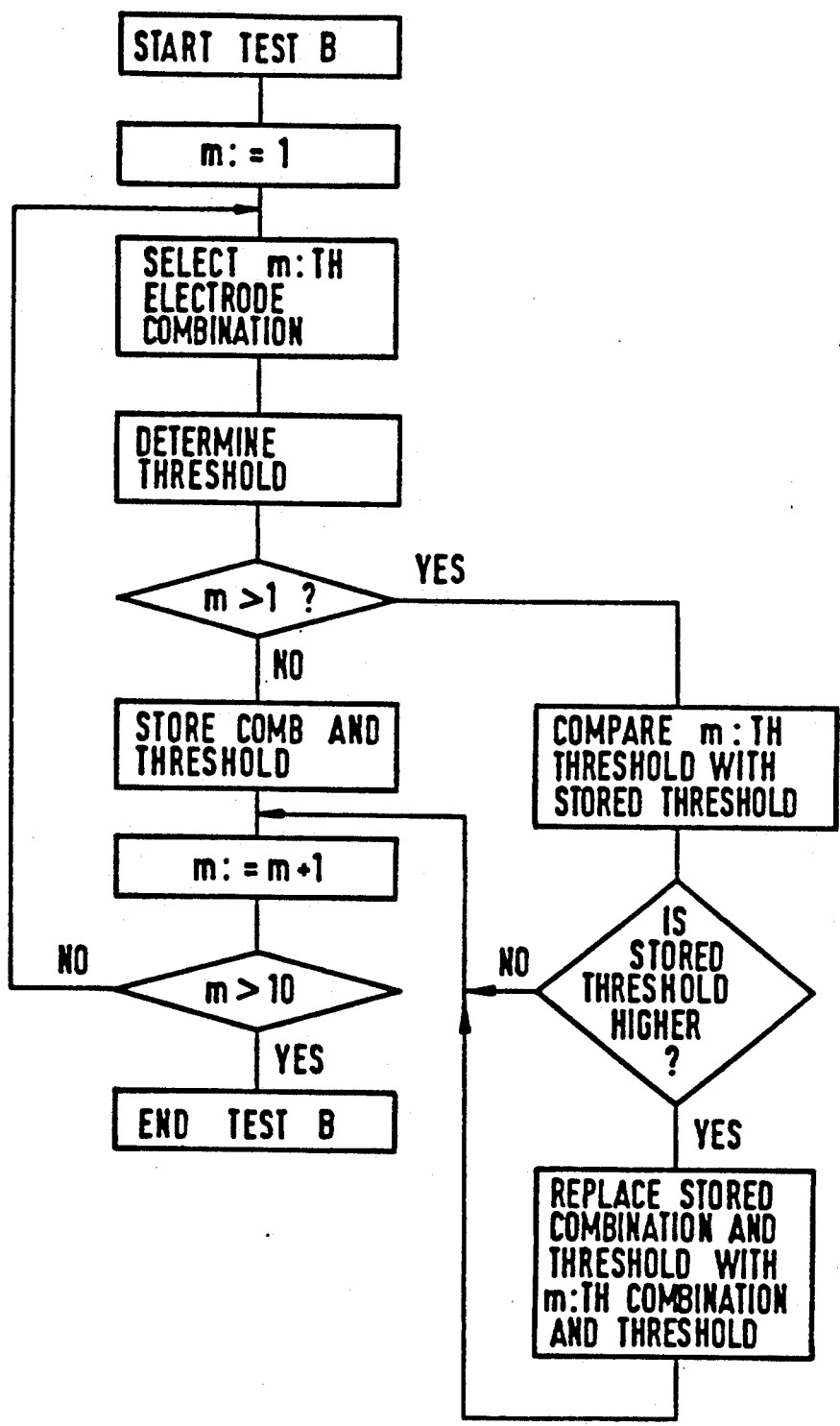

HEART STIMULATION APPARATUS

BACKGROUND OF THE INVENTION

1. Field of the Invention

The present invention relates to a heart stimulation apparatus for intracardial stimulation of heart tissue and/or sensing heart signals of the type having an electrode lead with an electrode head at the distal end thereof, the electrode head having at least first and second conductive surfaces for stimulating heart tissue and/or sensing heart signals respective connected to first and second separate conductors, the conductive surfaces being insulated from each other, and a stimulation pulse generator and/or a heart signal detector and a switch for connecting one conductive surface, or a plurality of the conductive surfaces, to the stimulation pulse generator and/or the detector in any desired manner.

2. Description of the Prior Art

A heart stimulation apparatus is disclosed in U.S. Pat. No. 4,628,934 in which an electrode lead can be provided with a plurality of independently connectable electrodes. The electrodes include a plurality of ring electrodes installed relatively far apart, and a conductive electrode tip. A switching stage is provided for connecting the electrodes in selected combinations to the pacemaker circuitry in a manner determined by a physician to be best suited for a given pacing function. Each electrode is individually tested to determine its capture threshold.

Another electrode device is known from U.S. Pat. No. 3,911,928 wherein a plurality of relatively small conductive surfaces are arrayed on the head of the electrode device in order to reduce the threshold value and also to reduce thus energy consumption. All the conductive surfaces on the head of this electrode device are connected to the same conductor. This can result in needlessly large energy consumption, since some of the conductive surfaces are not in contact with heart tissue for stimulation.

U.S. Pat. No. 4,760,852 describes a pacemaker electrode with a plurality of relatively large conductive surfaces connected to the same conductor disposed at a distal end of the electrode device.

SUMMARY OF THE INVENTION

It is an object of the present invention to provide a heart stimulation apparatus of the initially-described type with which an optimal threshold value for each patient, and therefore the lowest energy consumption is always attained. Another object is to provide such a heart stimulation apparatus wherein optimal sensing of heart signals is achieved.

The above objects are achieved in a heart stimulation apparatus constructed in accordance with the principles of the present invention having a switch, controlled by an autocapture function unit such that the respective conductive surfaces at the distal end of the electrode lead are automatically connected in different combinations, via their respective conductors, to the stimulation pulse generator in order to achieve optimal stimulation with minimized energy consumption.

As a result of this design for the heart stimulation apparatus, a combination of stimulation surfaces which provides the lowest stimulation threshold is automatically selected. As used herein, the term "combination of stimulation surfaces" encompasses a "combination" consisting of only one stimulation surface.

Preferably, at least one conductive surface serves as the stimulation electrode, and a different conductive surface serves as an indifferent electrode.

With, for instance, three conductive surfaces, a stimulation pulse may be delivered unipolarly via one of the surfaces, a combination of two surfaces or three surfaces, or bipolarly between two single surfaces or between a single surface and a double surface. The autocapture unit tests all possible combinations or a selected number of combinations programmed by a physician.

Further, the stimulation pulses could also be displaced in time and exhibit differed amplitudes at the different surfaces. This means that the duration of the pulses could vary, but it also means that a second pulse could arrive before a preceding pulse emitted. In this manner, a pulse can be given the exact morphology desired.

Analogously, by connecting the surfaces in different combinations to a heart signal detector, the sensing of heart signals can be made from the surfaces providing the lowest sensing threshold. The stimulation pulse generator and the heart signal detector can be referred to in common as circuits for performing cardiac-assist functions which are adjustable according to an electrical threshold of the cardiac tissue (the threshold possibly being different for the different cardiac assist functions, i.e., a stimulation threshold or a sensing threshold).

When stimulating bipolarly, preferably the conductive surface providing the lowest stimulation threshold is connected to a negative output of the stimulation pulse generator.

In an embodiment of the heart stimulation apparatus of the invention, the number and choice of conductive surfaces, connected via the conductor(s) to the detector for sensing, are selected independently of the conductive surface(s) employed for stimulation. This results in a large election of sensing surfaces on the electrode head. All conductive surfaces or the electrode head can be connectable to both the pulse generator and the signal detector, but a surface selected for use as a stimulation surface may then be inhibited, for a short time, from selection for use as a sensing surface. This is an advantage in sensing immediately after a stimulation, since the stimulating surface is then polarized at a relatively large voltage, and any sensing of the much lower level heart signals could be masked by the stimulation surface's polarization voltage.

In another embodiment of the invention, the conductive surfaces are uniformly distributed over the electrode head. In this way, one or more electrode surfaces would always be optimally placed against heart tissue.

In a further embodiment of the invention, the electrode head is hemispherical and the conductive surfaces are arrayed close to one another. In this manner, a relatively large number of conductive surfaces can be disposed on a very small electrode head. The shape of the electrode head ensures that heart tissue is not damaged.

In a preferred embodiment of the invention, the center of the electrode head has a projecting part with a conductive surface. Since the projecting part is extremely small, this part has at least a chance of retaining contact with heart tissue if the electrode head becomes dislocated.

In another version of this embodiment the invention, simple in design, the electrode head consists of at least two conductive bodies which are insulated from one another. With such a design, the electrode head can have a configuration in which one of the conductive bodies is displaced in relation to the other. The free end of the projecting part, in addition to the sides of the free end, can be insulated to prevent any conduction between the conductive surfaces of the bodies. As a result of the structure of the electrode head, the conductive surfaces of one body or another, or of both bodies, can be used for simultaneous stimulation of heart tissue and/or sensing of heart signals.

In another embodiment of the invention the electrode head is equipped with a traumatic fixing component on which at least one conductive surface is provided. This achieves both fixing of the electrode head to the heart wall and ensures that at least two conductive surfaces are in contact with heart tissue.

In an embodiment of the invention which is simple to construct, the fixing component is helical. In this way, the electrode head can be partially screwed into heart issue.

In another preferred embodiment of the invention, at east one of the conductive surfaces is made of a microporous material. As a result of the use of microporous material, the stimulation electrode and the indifferent electrode can be made very mall while the conductive surfaces are relatively large at the same time.

At least one of the conductive surfaces can also be coated with a layer of ion exchange material. The ion exchange material serves, e.g., as protection against contamination particles. The conductive surfaces are highly sensitive to such particles, particularly if the surfaces are made from a microporous material.

Additionally, a coating of medication can be applied on at least one of the conductive surfaces. This coating has an anti-inflammatory effect when the electrode head dresses against or is screwed into the heart wall. In this manner, formation of fibrous tissue around the electrode head, which otherwise could occur, is avoided or reduced.

DESCRIPTION OF THE DRAWINGS

FIG. 1 is a side view of a heart stimulation apparatus having an electrode device according to the invention, shown with an enlarged electrode head, partly in cross-section.

FIG. 2 is a block diagram illustrating the autocapture arrangement in more detail.

FIG. 3 illustrates in a flow chart for one possible autocapture routine which the heart stimulation apparatus may perform.

FIG. 4 illustrates in a flow chart for another possible autocapture routine which the heart stimulation apparatus may perform.

FIG. 5 is a frontal view of an electrode head according to FIG. 1.

FIG. 6 is a cross-section of the electrode device through the section line III-III in FIG. 1.

FIG. 7 is a side view of another embodiment of a heart stimulation apparatus having an electrode device according to the invention, with an enlarged electrode head shown in a cross section.

DESCRIPTION OF THE PREFERRED EMBODIMENTS

Figure 8:
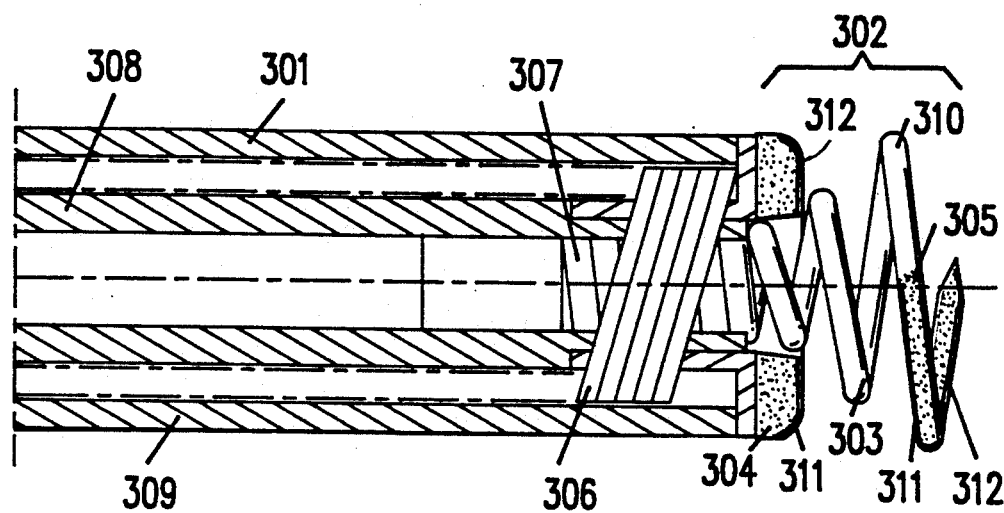
FIG. 8 is a side view of the distal end of the electrode device, shown in cross-section, according to the invention.

FIG. 1 depicts a heart stimulation apparatus 14 for intracardial stimulation of the heart tissue of a patient and/or sensing heart signals. The apparatus 14 includes an electrode device 1 containing an electrode cable 2 equipped with a hemispherical electrode head 3 at its distal end. The electrode head 3 is fitted with four round, closely spaced conductive surfaces 4, 5, 6 and 7 which are uniformly distributed on the electrode head 3 and which are electrically separated by insulating material 8. The conductive surface 7 is hidden, but can be seen in FIG. 2. Each conductive surface 4, 5, 6 and 7 is connected to its own elongate, flexible conductor 9, 10, 11 and 12 extending to the proximal end of the electrode cable. The conductors 9, 10, 11 and 12 are insulated from one another. The electrode cable 2 is also provided with an external layer of insulation 13. The heart stimulation apparatus 14 is connected to the proximal end of the electrode cable 2. The heart stimulation apparatus 14 further includes a switch unit 15 with four output terminals 16, 17, 18 and 19, respectively connected to conductors 9, 10, 11 and 12 for the conductive surfaces 4, 5, 6 and 7 on the electrode head 3. The switch unit 15 also has an electronics unit 20 connected to the output terminals 16, 17, 18, 19. The heart stimulation apparatus 14 additionally contains a stimulation pulse generator 21 and a detector 22 for sensing heart signals, each individually connected to the electronics unit 20, and an autocapture function unit 23 which is connected to the stimulation pulse generator 21, to the detector 22 and to the electronics unit 20.

FIG. 2 shows that the conductive surfaces 4, 5, 6 and 7 are uniformly arrayed on the electrode head 3. The conductive surfaces 4, 5, 6 and 7 are at the ends of wires consisting of a conductive material whose other ends are connected to one of the conductors 9, 10, 11 and 12, insulated from one another, as shown in cross-section through the electrode device in FIG. 3.

After the electrode cable 2 has been introduced into the patient's heart in a known manner and the electrode head is applied to heart tissue, the stimulation generator 21 is switched via the electronics unit 20, e.g., via output terminal 8 and conductor 11, to the conductive surface 6, a voltage for stimulating the heart tissue then being applied to the surface 6. The detector 22 is then switched in the same way, via the electronics unit 20, via one or more of the output terminals 16, 17, 18 and 19 and via the corresponding conductor 9, 10, 11 and/or 12, to one or more conductive surfaces 4, 5, 6 and/or 7 for sensing heart signals. The number and selection of conductive surfaces 4, 5, 6 and 7 connected to the detector 22, via one or more of the conductors 9, 10, 11 and 12, can be selected independently of the conductive surface(s) 4, 5, 6 and 7 employed for sensing. All conductive surfaces 4, 5, 6 and 7 can be switched for connection to the detector 22.

In FIG. 4 the circuitry in the heart stimulation apparatus 14 which executes the autocapture function and selection of electrode surface configuration is shown in a block diagram. The stimulation pulse generator 21, detector 22 and autocapture function unit 23 are, as also shown in FIG. 1, connected to the electronics unit 20. In the electronics unit 20 a first switch 121 is connected between the output terminal 16 and the stimulation pulse generator 21, a second switch 122 is connected between the output terminal 17 and the stimulation pulse generator 21, a third switch 123 is connected between the output terminal 18 and the stimulation pulse generator 21, a fourth switch 124 is connected between the output terminal 19 and the stimulation pulse generator 21, a fifth switch 125 is connected between the output terminal 16 and the detector 22, a sixth switch 126 is connected between the output terminal 17 and the detector 22, a seventh switch 127 is connected between the output terminal 18 and the detector 22, and an eighth switch 128 is connected between the output terminal 19 and the detector 22. The switches 121-128 an, when activated by the autocapture function unit 23, selectively connect any output terminal 16, 17, 18 and 19 or a combination of output terminals 16, 17, 18, 19 to the pulse generator 21 and/or detector 22 respectively. Further, a ninth switch 129 can connect neither, either or both of the stimulation pulse generator 21 and detector 22 to the case of the heart stimulation apparatus 14 for unipolar stimulation and sensing. The autocapture function unit 23 is programmed to automatically search for the conductive surface combination which results in the lowest stimulation threshold. This means that the autocapture function unit 23 will selectively, through the switches 121 to 129, test a sequence of different stimulation arrangements and select the most efficient one.

The autocapture function in itself is known (but not for use in the manner disclosed herein). Basically, it is performed by reducing the stimulation energy until there is no reaction from the heart, i.e., no capture, whereafter the stimulation energy is increased until a capture is detected by the detector 22 and the threshold is determined.

FIG. 5 illustrates one possible flow chart for performing a selection of the ten lowest thresholds of all programmed combinations. The number of possible combinations could be larger than the number of programmed combinations. This because it may, for instance, not be suitable to stimulate bipolarly between two conductive surfaces which are located too closely to each other.

The flow chart commences with the first block by starting TEST A and assigning the first combination (n:=1). The function will then proceed with the selection and connection of the first electrode combination, i.e., a first combination of conductive surfaces 4, 5, 6 and/or 7, and the threshold is determined for the first combination in a known manner. As this TEST A is intended to select the ten combinations having the lowest threshold, a decision block inquires whether the number n has exceeded ten selections. If not, the actual combination and threshold determined will be immediately stored and the number for the actual combination will be incremented by one (n:=n+1). In the next decision block it is determined whether all possible combinations N have been tested yet. If so, the test is ended and the ten combinations showing the lowest stimulation threshold will be stored in a memory. If TEST A has not run through all combinations, the next is selected and its threshold determined, etc.

When the number of tested combinations exceeds ten (YES in block n>10?), the determined threshold for the actual combination will be compared with the stored thresholds and if any stored threshold is higher than the currently determined threshold (YES in block IS STORED THRESHOLD HIGHER?) the stored combination will be replaced with the present combination and threshold. The number of tested combinations is now incremented and the function proceeds as described above.

It should be noted that this flow chart only indicates the rudiments of the autocapture function. If the number of possible combinations is large, it could be inconvenient for a patient if the heart stimulation apparatus were to run through all combinations in an uninterrupted sequence. In particular, the block DETERMINE THRESHOLD could therefore include timing functions reducing the number of tests per hour or the like. When no specific combination has been selected automatically the heart will be stimulated using either a combination and stimulation energy selected by a physician or a combination and stimulation energy previously chosen by the autocapture function.

FIG. 6 illustrates a flow chart for a TEST B. TEST B is a continuation of TEST A and in TEST B the stored ten combinations are tested to determine which of the ten has the lowest threshold. TEST B could be routinely performed by the heart stimulation apparatus 14 to ensure that the combination having the lowest threshold is permanently activated.

The flow chart begins with a START TEST B block, which could be initiated automatically at selected time intervals by the autocapture function unit 23. The first combination is then addressed (m:=1) and selected in the next block. As in TEST A the threshold is determined. In TEST B it is only relevant to find the combination having the lowest threshold, and the first threshold will therefore be stored to be compared with other combinations. In the next block the number for the combination is incremented and the function controls if all combinations have been checked, in which case TEST B is ended. Otherwise the next combination is selected and its threshold determined. The current combination and its threshold is now compared with the stored combination and threshold and if the stored threshold is higher, the current combination and threshold will replace the previously-stored combination and threshold, and the function proceeds by incrementing the number of combinations. If the stored threshold is lower than the actual threshold the function will only proceed to check out the next combination. When TEST B is ended the autocapture function unit 23 will use the selected combination until a new test may indicate that another combination is preferable, or when a physician by telemetry by means of an external programming unit selects a different combination for stimulation.

Analogously the autocapture function unit may select a combination of conductive surfaces 4, 5, 6 and/or 7 which provides the best sensing level for the detector 22.

It may be convenient if the block DETERMINE THRESHOLD in TEST B, as in TEST A, is provided with means for prolonging the entire test so that the execution of the test will be as unobstructive to the patient as possible.

There are other possible test routines which the autocapture function unit 23 may execute. For example, it may test all possible unipolar stimulation combinations and permanently select the conductive surface(s) providing the lowest threshold as stimulation electrode in a bipolar combination. The conductive surface(s) serving as stimulation electrode should in this connection be connected to a negative output of the stimulation pulse generator 21 as this will provide a lower threshold than if the stimulation electrode were to be connected to a positive output. Further, when connected bipolarly the autocapture function unit 23 may switch the connection so that the negative conductive surface(s) becomes positive and vice versa. The polarity change may be executed automatically if an increase in the threshold is detected by the autocapture function unit 23, thereby testing which of the two combinations provides the lowest threshold.

FIG. 7 shows a heart stimulation apparatus 224 with a function corresponding to the function shown and described in FIG. 1. An electrode device 225, whose design only differs from the previously illustrated and described electrode device 1 by having a different configuration for the electrode head, is connected to this heart stimulation apparatus 224. Thus, the electrode device 225 contains a cable 226 at whose distal end an electrode head 227 is provided. The electrode head 227 consists of two conductive bodies 228 and 229 which are electrically insulated from one another by a layer of insulation 230. The center of the body 228 is equipped with a through opening in which the body 229 is inserted. The bodies 228 and 229 are also displaced in relation to one another so the center of the electrode head 27, as seen from the side, has a projecting part formed by the body 229, the side of the partially free end of this body 229 having a conductive surface 231. The free surface of the body 228 forms a second conductive surface 232. Since the insulation 230 covers the body 229, in addition to the end side, no electrical conduction can occur between the conductive surfaces 231 and 232. These conductive surfaces 231 and 232 are respectively connected to elongate, flexible, insulated conductors 233 and 234 extending to the proximal end of the electrode cable 226 and being connected to respective output terminals 235 and 236 on a switch 237. The switch 237 also contains an electronics unit 220 which functions analogously to the previously described electronics unit 20. The electronics unit 220 is, in turn, connected to a stimulation pulse generator 221, a heart signal detector 222 and a function unit 223 for autocapture. The electrode cable 226 is also provided with an external layer of insulation 238. As a result of the described electrode device with its electrode head 227, either the conductive surface 231 or the conductive surface 232, or both surfaces 231 and 232 in combination, can be used for stimulating a patient's heart tissue and/or sensing heart signals.

FIG. 8 shows the distal end of a bipolar electrode device for intracardial stimulation of heart tissue in a patient. The electrode device contains an electrode cable 301 at whose distal end an electrode head 302 with a helical fixing device 303 is installed. The electrode head 302 is provided with two conductive surfaces 304 and 305, respectively connected to elongate conductors 306 and 307 which run inside the electrode cable 301 and extend to the proximal end of the electrode cable. The conductors 306 and 307 are insulated from one another by a layer of insulation 308. The electrode cable 301 is also provided with an external layer of insulation 309. FIG. 8 shows that one of the conductive surfaces 305 can be provided on the anterior end of the fixing device 303, and the rest of the fixing device is provided with an insulating surface coating 310, the conductive surface 304 forming a ring around the seat of the fixing device 303. The conductive surfaces 304 and 305 are made of a microporous material, such as titanium nitride. To protect these surfaces 304 and 305 from contaminating particles, the surfaces 304 and 305 are coated with a layer of ion exchange material 311 which, in this embodiment, is in turn coated with a layer of medication 312 for providing, e.g., an anti-inflammatory effect when the electrode is implanted. The conductors 306 and 307 for the conductive surfaces 304 and 305 can be connected optionally to different poles in a pacemaker (not shown) in such a way that conductive surface 304, for example, serves as an indifferent electrode and conductive surface 305 serves as a stimulation electrode. When necessary, the conductive surface 305 can serve as the indifferent electrode and the conductive surface 304 be used as the stimulation electrode.

Figure 9:
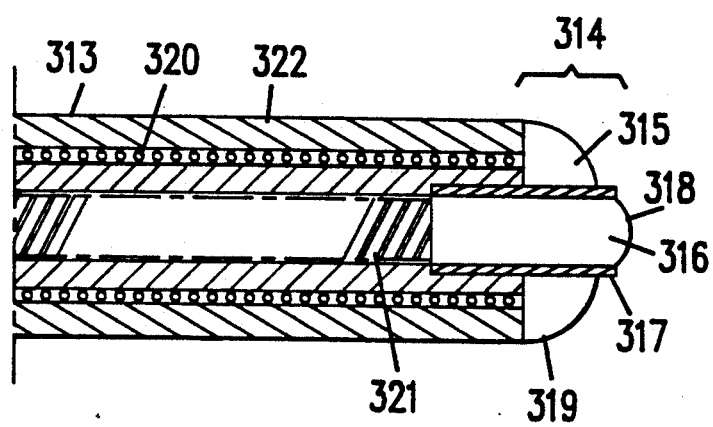
FIG. 9 is a side view of another embodiment of the distal end of the electrode device, shown in cross-section, according to the invention.

FIG. 9 shows a non-traumatic electrode device containing an electrode cable 313 at whose distal end an electrode head 314 is installed. The electrode head 314 is formed by two conductive bodies 315 and 316 which are electrically insulated from one another by a layer of insulation 317. The center of the body 315 is provided with a through opening in which the body 316 is installed. The bodies 315 and 316 are uniformly displaced in relation to one another so the center of the electrode head 314, seen in profile, has a protruding part formed by the body 316, the partially free end side of this body consisting of a conductive surface 318. The free surface of the body 315 forms a second conductive surface 319. The conductive surfaces 318 and 319 are respectively connected to an elongate, flexible, individually insulated conductor 320 and 321 which run to the proximal end of the electrode cable 313. The electrode cable 313 is also provided with an external layer of insulation 322. With the electrode device and its electrode head 14, as described in FIG. 9, either the conductive surface 318 or the conductive surface 319 can be connected to a pacemaker in such a way that either, as described in connection with FIG. 8, can serve as an indifferent electrode or as a stimulation electrode. Conductive surfaces 318 and 319, which are made of a microporous material, can, like conductive surfaces 304 and 305 in FIG. 8, be coated with an ion exchange material and with a layer of medication, although this is not shown in FIG. 9.

The electrode head of the electrode device according to the invention is not limited to the described embodiments. Any configuration can be used wherein the conductive surfaces on the electrode head are electrically insulated from one another, so that one or a desired combination of several conductive surfaces can be used for attaining optimal stimulation with minimal energy consumption. The number of conductive surfaces is not limited. In addition, the size and shape of all or some of the surfaces can vary.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for intracardial electrical interaction with cardiac tissue, comprising:
    an electrode lead having an electrode head disposed at a distal end thereof, said electrode head having a plurality of separate electrically conductive electrode surfaces thereon electrically insulated from each other and adapted for in vivo electrical interaction with cardiac tissue, and a like plurality of electrical conductors respectively connected to said electrode surfaces, said electrical conductors being electrically insulated from each other and extending through said electrode lead to a proximal end thereof;

circuit means for performing an energy-consuming cardiac-assist function which is adjustable according to an electrical threshold associated with said cardiac-assist function;

switch means disposed between said proximal end of said electrode lead and said circuit means for connecting a combination of said electrical conductors to said circuit means for activating the respective electrode surfaces connected to said electrical conductors in said combination for use in performing said cardiac-assist function; and autocapture means for controlling said switch means by selecting said combination of conductors to connect to said circuit means based on said electrical threshold for optimizing said cardiac-assist function and minimizing the energy consumption of said cardiac-assist function.

2. An apparatus as claimed in claim 1 wherein said circuit means comprises means for generating stimulation pulses, and wherein said electrical threshold comprises the stimulation threshold of said cardiac tissue.

3. An apparatus as claimed in claim 2 wherein said autocapture means comprises means for controlling said switch means for selecting a combination of said electrical conductors for activating at least one of said plurality of electrode surfaces for use as a stimulation electrode, and for activating a different one of said electrode surfaces for use as an indifferent electrode.

4. An apparatus as claimed in claim 2 wherein said means for generating stimulation pulses has a negative output and wherein said autocapture means comprises means for identifying one of said plurality of electrode surfaces as having a lowest stimulation threshold and for controlling said switch means to connect the identified one of said electrode surfaces having said lowest stimulation threshold to said negative output of said stimulation pulse generator.

5. An apparatus as claimed in claim 2 wherein said circuit means further comprises detector means for sensing electrical heart signals and wherein said electrical threshold further comprises a sensing threshold of said detector means.

6. An apparatus as claimed in claim 5 wherein said autocapture means comprises means for selecting a combination of conductors for connection to said means for generating stimulation pulses independently of selecting a combination of conductors for connection to said detector means.

7. An apparatus as claimed in claim 5 wherein said autocapture means comprises means for selecting a combination of conductors for connecting all of said electrical conductors to said detector means for activating all of said electrode surfaces for use in sensing said electrical heart signals.

8. An apparatus as claimed in claim 1 wherein said electrode head consists of at least two electrically conductive bodies which are electrically insulated from each other, and wherein at least one of said electrode surfaces is carried on each of said conductive bodies.

9. An apparatus as claimed in claim 8 wherein one of said conductive bodies has a central opening therein and a conductive surface on which said at least one of said electrode surfaces is disposed, and wherein another of said conductive bodies is disposed in said opening with a portion thereof projecting from said opening beyond said conductive surface.

10. An apparatus as claimed in claim 1 wherein said electrode head has a traumatic fixing element thereon for fixing said electrode head to cardiac tissue, said traumatic fixing element having at least one conductive surface thereon forming one of said electrode surfaces.

11. An apparatus as claimed in claim 10 wherein said traumatic fixing element is helical.

12. An apparatus as claimed in claim 1 wherein said electrode surfaces are uniformly disposed on said electrode head.

13. An apparatus as claimed in claim 1 wherein said electrode head is hemispherical and wherein said electrode surfaces are disposed close to each other on said electrode head.

14. An apparatus as claimed in claim 1 wherein at least one of said electrode surfaces consists of microporous material.

15. An apparatus as claimed in claim 14 wherein said at least one of said electrode surfaces consisting of microporous material is covered with a layer of ion exchange material.

16. An apparatus as claimed in claim 1 wherein at least one of said electrode surfaces comprises a medication layer coating.

* * * * *